United States Patent [19]
Venter et al.

[11] Patent Number: 6,151,972
[45] Date of Patent: Nov. 28, 2000

[54] URINE SAMPLING DEVICE

[75] Inventors: Jacob Cloete Venter, Sedgefield; Karel David Venter, Paarl, both of South Africa

[73] Assignee: V&N Projects CC, South Africa

[21] Appl. No.: 09/254,814

[22] PCT Filed: Sep. 12, 1997

[86] PCT No.: PCT/GB97/02500

§ 371 Date: May 3, 1999

§ 102(e) Date: May 3, 1999

[87] PCT Pub. No.: WO98/10702

PCT Pub. Date: Mar. 19, 1998

[30] Foreign Application Priority Data

Sep. 13, 1996 [ZA] South Africa ............................ 96/7715
Oct. 18, 1996 [ZA] South Africa ............................ 96/8789

[51] Int. Cl.[7] ............................... G01N 1/20; G01N 1/00; A47K 11/00
[52] U.S. Cl. ..................................... 73/863.41; 73/863.52; 4/144.1; 4/144.2; 4/144.3; 604/319; 604/329
[58] Field of Search ........................... 73/863.41, 863.52; 4/144.1, 144.2, 144.3; 604/319, 329

[56] References Cited

U.S. PATENT DOCUMENTS

| | | |
|---|---|---|
| 2,801,424 | 8/1957 | Mercer ..................................... 4/144.1 |
| 3,501,781 | 3/1970 | Ott . |
| 4,137,573 | 2/1979 | Kroeger . |
| 4,252,132 | 2/1981 | Kuntz ...................................... 128/761 |
| 5,060,317 | 10/1991 | Bertelsen . |
| 5,146,637 | 9/1992 | Bressler et al. . |
| 5,625,911 | 5/1997 | Nakayama et al. ........................ 4/661 |

*Primary Examiner*—Hezron Williams
*Assistant Examiner*—Dennis Loo
*Attorney, Agent, or Firm*—Ostrolenk, Faber, Gerb & Soffen, LLP

[57] ABSTRACT

A urine sampling device (1) which facilitates urine sampling of female and infirm patients which is adapted to be associated with a toilet bowl (2) to collect a sample while the patient passes urine while seated on the toilet, wherein the urine sampling device (1) comprising an elongated trough member having a width substantially greater than its depth to define a generally pan-like trough, the trough member being fitted at a first end thereof with an attachment formation (3) by means of which the device (1) may in use be mounted in the toilet bowl (2) so that the trough member extends at a suitable angle to the horizontal so as to intercept a stream of urine being passed by a patient seated on the bowl (2), and also so as to minimise splashing of such urine onto the patient, the device (1) further including a urine sample collecting arrangement (4, 5).

5 Claims, 2 Drawing Sheets

URINE SAMPLING DEVICE

This invention relates to urine sampling devices.

It is an object of this invention to provide a urine sampling device which is particularly useful in collecting urine samples from female patients but which may also be used for collecting urine samples from infirm and young patients.

One example of a known urine collection device is that disclosed in U.S. Pat. No. 5,146,637. This comprises a body having sidewalls and a bottom which is suspended across the entire width of the toilet bowl by three arms which extend over the rim of the toilet bowl. The bottom of the device if funnelled to an outlet. A support is provided below the outlet to support the upper rim of a collecting cup. In use, urine is received in the collection device, and this is funnelled through the outlet and into a collecting cup supported below the outlet.

An alternative urine collection device is disclosed in U.S. Pat. No. 5,060,317. This comprises a bracket mounted to the rim of the toilet bowl and including a hole for receiving a sample cup. In use, the sample cup is supported within the toilet bowl by the bracket, and collects urine. A handle is then used to remove the sample cup from the bracket. U.S. Pat. No. 4,137,573 also discloses the use of a bracket mounted to the toilet bowl for receiving a sample cup to collect urine.

According to the present invention a urine sampling device comprises an elongated trough member having a width substantially greater than its depth to define a generally pan-like trough, the trough member being fitted at a first end thereof with an attachment formation arranged to engage the rim of a toilet bowl such that, in use, the trough member extends at an angle below the horizontal such that the trough is orientated to intercept a stream of urine being passed by a patient seated on the bowl, and to minimise splashing of such urine onto the patient, the device further including a urine sample collecting arrangement disposed at or towards the extremity of the trough remote from the first end thereof, and having an overflow lip through which surplus urine not collected by the collecting arrangement is discharged into the toilet bowl.

Thus the collecting arrangement may comprise a hollow spigot extending downwardly from the trough member to define a passage and onto which hollow spigot a pathology sample bottle may temporarily be mounted in use.

In another form of the invention the collecting arrangement may comprise a liner for the sampling device. The liner in issue may be shaped to be mounted in the trough-shaped sampling, device and be adapted to be lifted from the sampling device to contain the urine sample for analysis. Preferably the liner defines a well region adapted in use to be received in an appropriately shaped and located depression in or passage through the trough.

The liner may be made from any suitable polymeric material.

In a preferred arrangement according to this form of the invention there is provided a pack of liners of the type in issue which may be placed in the trough-shaped sampling device to be individually peeled from the pack as and when required.

DETAILED DESCRIPTION OF INVENTION

In the accompanying drawings of non-limiting, examples which serve to illustrate the invention:

The same reference numerals are used to indicate corresponding components in the accompanying drawings.

Figure 3:
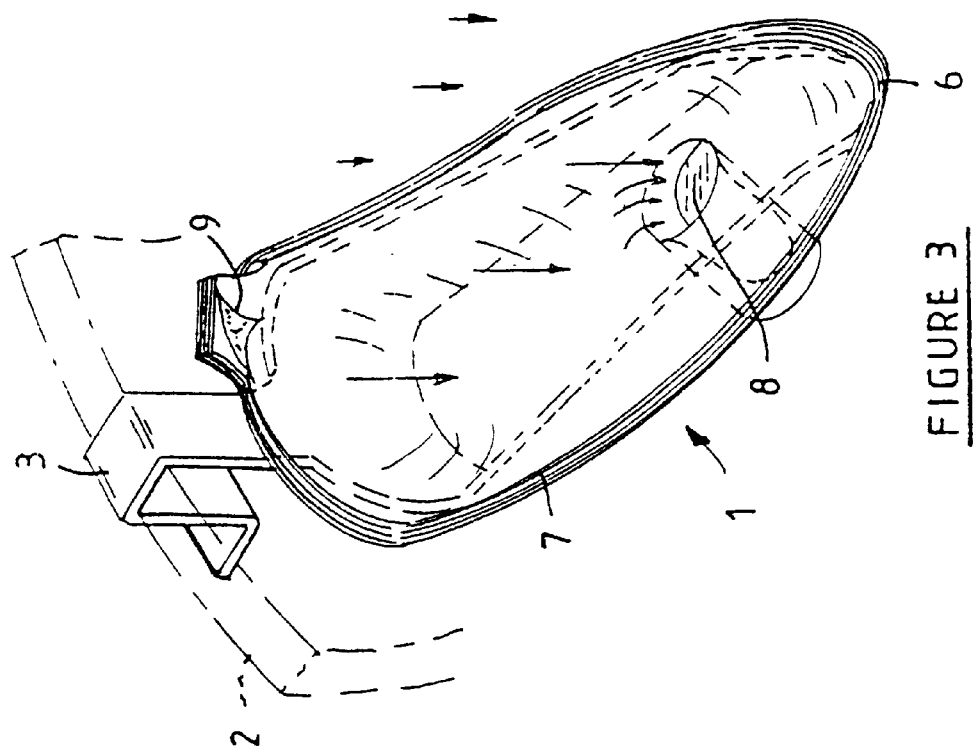
FIG. 3 is a schematic perspective view of an alternative embodiment of the invention.

In the drawings a trough-shaped urine sampling device 1 is shown to be fitted to the rim of a toilet bowl 2 [indicated in dotted lines in FIG. 3 at 2] by means of a clip formation 3 forming part of the sampling device. The trough and clip formation are preferably so shaped as to allow it to be mounted so that the trough extends at an angle of more or less 30° below the horizontal into the bowl. By so mounting the device the patient may urinate normally from a seated position on the toilet bowl and the device would serve to intercept the stream of urine to direct a sample thereof towards its free end opposite the clip 3.

The clip formation may be adapted snugly to engage a variety of toilet bowl configurations and may for this purpose comprise an associated spacer element which may optionally be used when required.

Figure 1:
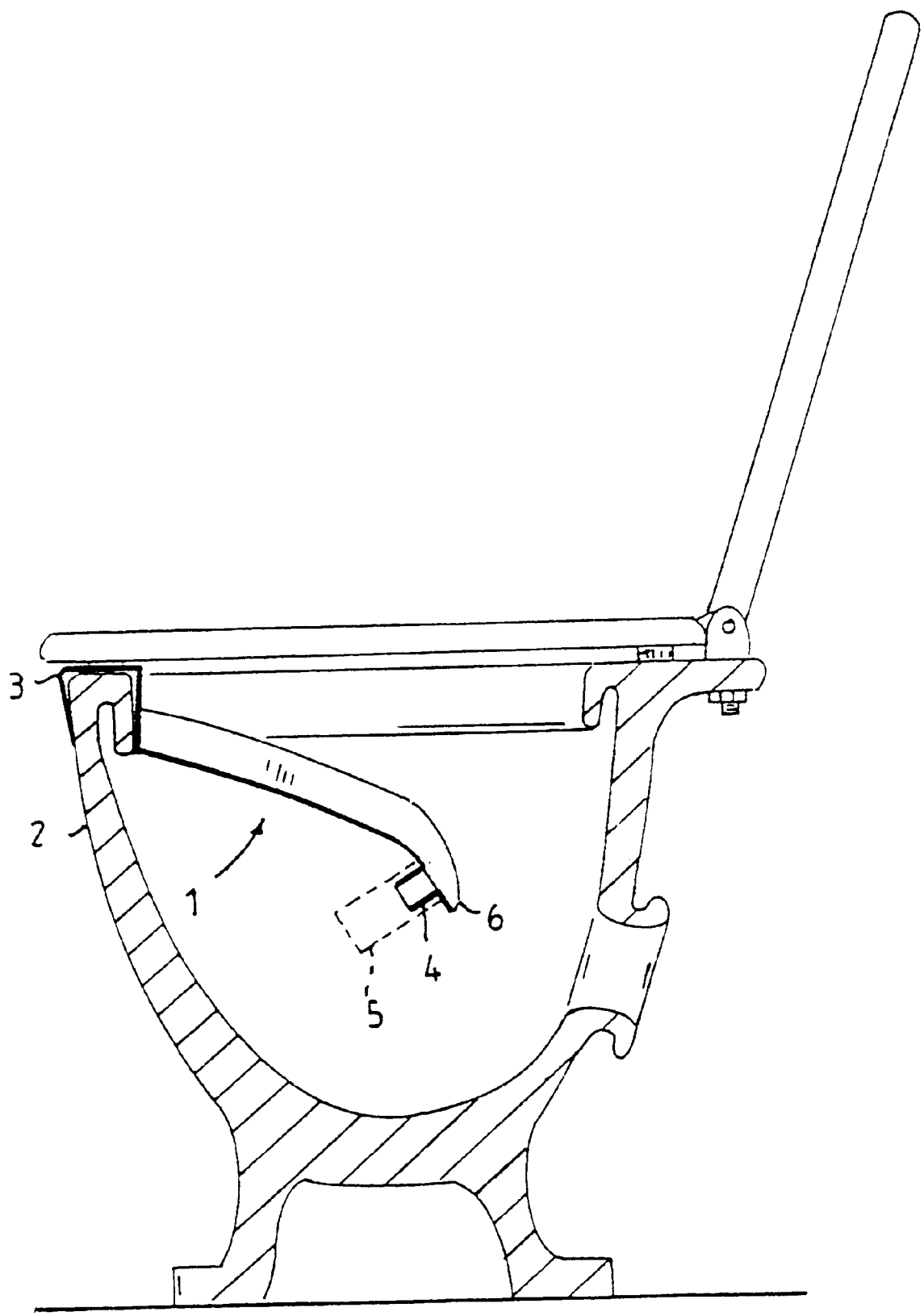
FIG. 1 is a cross-sectional side view through a toilet bowl, with seat and cover onto which bowl the urine sampling device of the invention is shown to be fitted.
Figure 2:
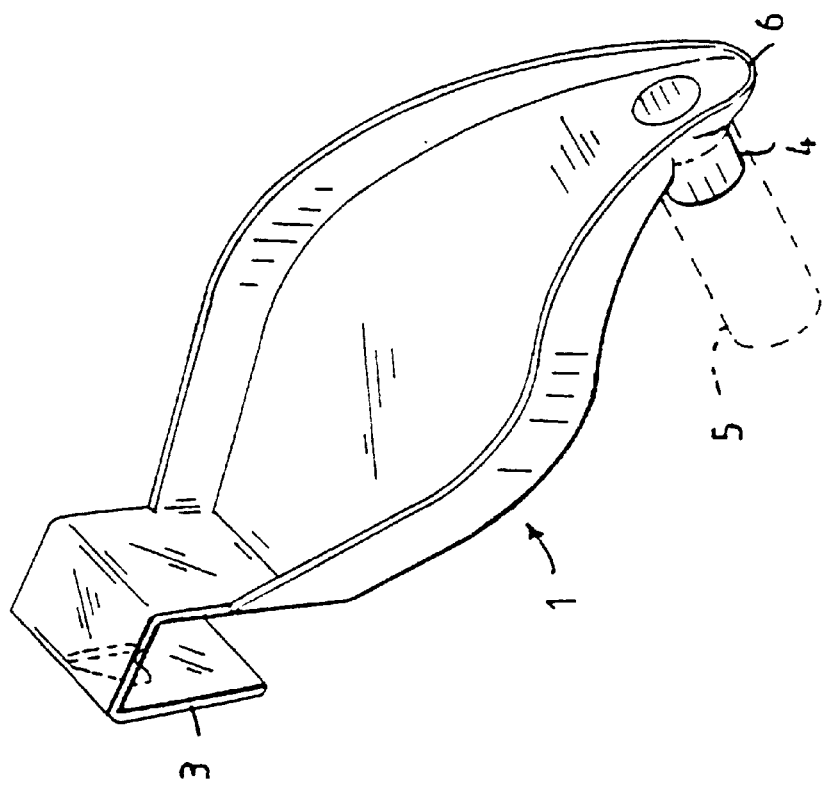
FIG. 2 is a schematic perspective view of a first embodiment of the urine sampling device of the invention.

The trough is provided towards its end opposite to the clip 3 with a hollow spigot 4 onto which spigot a pathology sample bottle 5 may be mounted as shown in FIGS. 1 and 2. The spigot may be tapered to be capable of receiving pathology bottles of difference internal mouth diameters or may present tapering ribs on the exterior thereof for this purpose.

The free end of the trough defines an overflow lip 6 through which any surplus urine may in use be discharged into the toilet bowl.

In the embodiments illustrated in FIGS. 1 and 2 the sampling device is preferably made by injection moulding of a polymeric material rendering it capable of being autoclaved to a temperature of 135° C. for sterilization purposes. It can also be produced from a suitable metal such as stainless steel.

In the drawing of FIG. 3 a pack of liners 7 is shown to be fitted on the sampling trough. The liners may be made from any pathologically acceptable polymeric sheet material. Each liner is shaped to define a well formation 8 into which a sample of urine may in use be received when a patient urinates onto the trough as described above. The necessary pathologic tests may then be conducted on the collected sample, e.g. by placing the dip-stick type diagnostic strip directly into the urine in such well.

After use the urine may be discarded and the used liner may simply be stripped from the pack by means of the tab 9 provided for that purpose, thereby to expose a sterile new liner and hence rendering the device ready for re-use without the need to sterilise it in other ways.

Clearly many variations of the invention may be devised without thereby departing from the spirit of the invention. Thus the pack of liners may be kept in a separate dispenser from which individual liners may be dispensed when required and placed in the sampling device as and when required.

We claim:

1. A urine sample device comprising an elongated trough member having a width substantially greater than its depth to define a generally pan-like trough, the trough having a first end thereof fitted with an attachment formation arranged to engage a rim of a toilet bowl such that, in use, the trough is oriented to intercept a stream of urine being passed by a patient seated on the bowl, a urine sample collecting arrangement comprising a liner for the sampling device, the collecting arrangement being disposed at or towards the extremity of the trough and remote from the first end of the trough, and the arrangement having an overflow lip through which surplus urine not collected by the collecting arrangement is discharged into the toilet bowl.

2. The device according to claim 1, wherein the liner is shaped to be capable of being mounted in the trough and adapted to be lifted from the trough to contain the urine sample for analysis.

3. The device according to claim 1, wherein the trough includes a depression or passage; the liner defines a well region adapted in use to be received in the appropriately shaped and located depression in or passage through the trough.

4. The device of claim 1, wherein the liner is made from any suitable polymeric material.

5. The device of claim 3, wherein there is provided a pack of the liners in which may be placed in the trough to be individually peeled from the pack as and when required.

\* \* \* \* \*